United States Patent [19]
Sanford et al.

[11] 4,333,733
[45] Jun. 8, 1982

[54] CONTINUOUS RELEASE OF REAGENT IN AN ANALYTICAL ELEMENT TO REDUCE ASSAY INTERFERENCE

[75] Inventors: Karl J. Sanford; Jon N. Eikenberry, both of Rochester, N.Y.

[73] Assignee: Eastman Kodak Company, Rochester, N.Y.

[21] Appl. No.: 169,704

[22] Filed: Jul. 17, 1980

[51] Int. Cl.³ .............. G01N 21/78; G01N 31/22; G01N 33/68
[52] U.S. Cl. .............. 23/230 B; 23/230 R; 23/902; 422/56; 422/57
[58] Field of Search .............. 422/56, 57, 58; 23/230 R, 230 B, 902

[56] References Cited

U.S. PATENT DOCUMENTS

| | | | |
|---|---|---|---|
| 3,485,587 | 12/1969 | Keston | 23/230 |
| 3,533,749 | 10/1970 | Kleinman | 23/230 |
| 3,723,064 | 3/1973 | Liotta | 422/56 X |
| 3,992,158 | 11/1976 | Przybylowicz et al. | 23/253 |
| 4,042,335 | 8/1977 | Clement | 23/253 |
| 4,132,528 | 1/1979 | Eikenberry et al. | 23/230 |
| 4,153,668 | 5/1979 | Hill et al. | 422/57 X |

OTHER PUBLICATIONS

Gustafsson, *Clin Chem*, vol. 22, No. 5, p. 616 (1976).
Ingwerson and Raabo, *Clin Chim Acta*, vol. 88, p. 545 (1978).
Webster, *Clin Chem*, vol. 23, No. 4, p. 663 (1977).

*Primary Examiner*—Arnold Turk
*Attorney, Agent, or Firm*—J. Jeffrey Hawley

[57] ABSTRACT

Analytical elements and methods for the selective determination of an analyte in aqueous fluids containing the analyte. These elements and methods feature means for continuously releasing chromogenic indicator reagent from a reagent zone to a reaction zone. The continuous release means is responsive to the application of a sample of the fluid to continuously release reagent into the reaction zone at a rate producing color response corresponding to interaction of the indicator with the analyte and reduced interaction of the indicator with interferents. In preferred embodiments, albumin is determined in the presence of interfering proteins such as globulins using buffered chromogenic indicator reagent. In such embodiments, when protein interferents are present, their interference can be substantially eliminated for up to three minutes, during which time color response is substantially only from the interaction of albumin and reagent. The determination of albumin follows from such color response.

27 Claims, No Drawings

CONTINUOUS RELEASE OF REAGENT IN AN ANALYTICAL ELEMENT TO REDUCE ASSAY INTERFERENCE

BACKGROUND OF THE INVENTION

1. Field of the Invention

The present invention relates to multizone dry chemistry analytical elements for the determination of an analyte, such as albumin, in aqueous fluids, and to methods for the use of such elements. In particular, the invention relates to the continuous release within such elements of a chromogenic indicator reagent composition to a reaction zone to thereby eliminate or reduce interference from competing substances, if present.

2. Discussion Relative to the Prior Art

In the analytical determination for analytes in aqueous fluids such as urine and serum or other body fluids, chromogenic indicator reagent compositions that interact with such analytes to produce a color response are frequently employed. The color response is then compared with appropriate standards or calibrators to determine the quantity of analyte present in the fluid.

In many instances, interfering substances accompany the analytes and interact with the reagent composition to produce a color response bearing the same color absorption characteristics as those produced by the analyte reagent interaction. The analyte-reagent and interferent-reagent interactions are additive resulting in a biased overall color response from which the component attributable to analyte-reagent interaction cannot readily be discerned. For example, in the determination of magnesium in aqueous fluids by interaction with chromogenic indicators such as Eriochrome ® Black T (EBT) or Titan yellow dye to produce a characteristic color response, calcium is a potential interferent. If present, calcium also interacts with either dye to produce a biased color response. Similarly, in the determination of albumin in body fluids by interaction of albumin with buffered chromogenic indicator reagents to produce a color response, accompanying protein interferents such as globulins or transferrin also interact with the reagent to produce a biased color response.

The concern for reducing interference to analyte assays using chromogenic indicator reagents applies to many assays. For the purpose of illustration, the prior art and background relative to albumin assays is set forth below.

Albumin is the most abundant of plasma proteins, generally constituting slightly over half of the total protein in the plasma. Albumin has a molecular weight of about 69,000, is synthesized in the liver, and has a half-life of about four weeks. It has two important roles:

(a) regulating the water balance between blood and tissues, and (b) functioning as a transport molecule for various materials which are only slightly soluble in water, such as bilirubin, fatty acids, cortisol, thyroxine, and a number of drugs including sulfonamides and barbiturates.

It is frequently important to determine whether patients have a deficiency of serum albumin. A deficiency of albumin in a patient's serum indicates a possibility of edema, nephrosis, cirrhosis, multiple sclerosis, hepatitis and other disease states. Also, albumin deficiency interferes with the transport of insoluble materials. Thus, albumin levels in body fluids are a useful tool for diagnosing illness. Accordingly, there is a need for procedures and materials which detect and quantify albumin, particularly low values of albumin in body fluids.

The determination of albumin in fluids is now widely practiced using buffered bromcresol green (hereinafter referred to as BCG) solutions or test strips as disclosed in U.S. Pat. No. 3,533,749 issued Oct. 13, 1970 to N. Kleinman and U.S. Pat. No. 3,485,587 issued Dec. 23, 1969 to A. S. Keston. Bromcresol green (BCG) is a sulphonphthalein species of chromogenic indicator materials that exhibit a color response, i.e., a change in color, by dye-binding interaction with proteins such as albumin. Such color response is proportionally related to the amount of albumin present. As noted above, the indicators are buffered which insures against color response to pH changes to which the indicators are otherwise sensitive.

Chromogenic indicators such as BCG are not entirely specific to albumin. Globulins, transferrin and other proteins normally present, for example, in human biological fluids compete for dye binding with the indicator causing interference to albumin assays. The interference is particularly significant with albumin at low concentration levels. For example, the normal total protein content, including albumin and globulin, of human serum ranges from about 6–8 g/dL. Of this, about 2.9 g/dL represents globulins, the balance being predominantly albumin. In normal serum (i.e., from healthy individuals), the albumin-to-globulin ratio is about 1.6:1 while in disease states the ratio may drop to about 0.7:1. A useful clinical assay must therefore avoid binding with globulins and result in a selective binding with albumin.

Several authors have suggested solutions to the problem of non-specificity in BCG-based albumin determinations. In 1976, J. C. Gustafsson reported that the reaction of serum albumin with BCG is faster than the reaction of BCG with other proteins. (Gustafsson, J. E. C., Clin Chem., 22:616, 1976). Accordingly, Gustafsson proposed to measure the absorbance of the solution twice after serum is mixed with BCG reagent: immediately and at 60 minutes. The immediate reading when extrapolated back to zero minutes is then employed to determine the albumin concentration. (The sixty minute reading is employed in the determination of serum protein components in addition to albumin.) The success of this method is predicated on the capability of one being able to obtain an "immediate" absorbance reading, an impractical requirement for automated systems that have inherent time lags of one or more minutes before meaningful readings can be taken. The Gustafsson zero minute procedure, moreover, is applicable to solution assays wherein for example, 10 μL of serum is interacted with 2.0 ml (2000 μL) of BCG reagent solution, a 200-fold dilution. However, with the advent of dry chemistry analytical assay elements, dilution of samples and the use of space-consuming liquid reagents are no longer required. In use, such elements are contacted with undiluted body fluids to produce a color response. The present inventors have determined, in this regard, that in undiluted samples, the total protein-BCG color response, i.e., the response from both albumin and globulins, is significantly more intense than in solution assays. Accordingly, zero minute determination of albumin in dry elements using the procedure of Gustafsson is not only impractical, but less specific to albumin compared to solution assays.

D. Webster (Clin. Chem., 23:663, 1977) confirmed the non-specificity of the BCG-based albumin determination for solution assays. That author concluded that a reading taken within 30 seconds was specific to albumin when 3.0 g/liter is subtracted from the result obtained. As in the Gustafsson procedure, Webster's method is predicated on early read times and an assay in dilute solution (200-fold dilution of sample fluids). The use of an arbitrary constant as a correction factor assumes, moreover, that the albumin result is overstated from the outset and so signifies a non-specific assay. More important, it does not account for real variations from the arbitrary 3.0 g/liter factor.

After Webster and Gustafsson, the problem of non-specificity of the BCG-based albumin assay was further disclosed by Ingwersen, S. and Raabo, E., Clin. Chim, Acta, 88:545, 1978. Ingwersen at al. determined that in dilute systems such as those studied by Gustafsson and Webster, lowering the concentration of BCG in the reagent solution suppressed the binding of globulins to such a degree that a reading could be taken as late as one minute after addition of the reagent. This reading was reported to be almost entirely due to the albumin-BCG complex.

The method according to Ingwerson et al. permits a reading to be taken up to one minute after initiation of the assay in solution. However, the present inventors have determined that when BCG indicator is used in conventional dry analytical elements in amounts suggested by Ingwersen, severe interference from competing proteins such as globulins is encountered. Still further, the interference is observed immediately, i.e., within less than one minute, thus emphasizing the distinction between dilute solution systems and dry chemistry systems employing undiluted serum.

If one were to consider lowering further the amount of BCG indicator in dry analytical elements in order to reduce the aforementioned globulin interference, it would generally not be possible without loss in sensitivity and linearity of response to anticipated levels of albumin, particularly high (e.g., 5 g/dL or higher) albumin levels.

The use of analytical elements for the determination of protein is well known. In the aforementioned Keston U.S. Pat. No. 3,485,587, single zone elements that include absorbent paper impregnated with buffered indicator reagent such as BCG are proposed. In use, the element is saturated with a sample of body fluid causing instantaneous contact of all the reagent with fluid to initiate color development. Such elements are useful to detect the presence or estimate the quantity of total protein. They cannot, however, accurately selectively determine albumin in the presence of globulins because, as previously noted, globulins compete for available indicator.

Multizone elements for the determination of analytes (including albumin) are disclosed in U.S. Pat. No. 3,992,158 issued Nov. 16, 1976 to E. P. Przybylowicz and A. G. Millikan and U.S. Pat. No. 4,042,335 issued Aug. 16, 1977 to P. L. Clemént. In U.S. Pat. No. 3,992,158, FIG. 2 therein depicts a porous spreading layer on a reagent layer overlying a support. Numerous matrix materials such as gelatin, agarose and water soluble vinyl polymers, are disclosed as useful in the reagent layer. In use, the spreading layer of elements according to U.S. Pat. No. 3,992,158 is contacted with an aqueous sample which distributes uniformly throughout the spreading layer and into the reagent layer. In the reagent layer, a material interacts with an analyte in the sample to produce a detectable change. This patent further discloses that the element may be readily adapted for use in the analysis of analytes such as albumin by appropriate choice of test reagents or other interactive materials. Neither BCG or similar reagents, nor the problem of interference to an analyte assay using chromogenic indicator reagent is disclosed in this patent.

Multizone elements for the determination of total protein are disclosed in U.S. Pat. No. 4,132,528 issued Jan. 2, 1979 to J. N. Eikenberry et al. Such elements are composed of a spreading zone for distributing analyte containing fluid and a reagent zone composed of reagent, an alkaline-providing composition, and an alkaline-protective polymer. Alkaline-protective polymers include poly(vinylpyrrolidone), poly(acrylamide), agarose and copolymers of vinylpyrrolidone and acrylamide. The reagent employed to quantitate total protein is a modified biuret composition which interacts indiscriminately with albumin and other proteins. Unlike the present invention which, in one embodiment, selectively determines albumin in the presence of protein interferents, the invention disclosed in U.S. Pat. No. 4,132,528 can only determine total protein by virtue of the reagent employed.

SUMMARY OF THE INVENTION

In the present invention, selective determination of an analyte in aqueous fluids containing the analyte and possible interferents to an assay for the analyte is carried out in a multizone dry analytical element containing a chromogenic indicator reagent. According to the invention, chromogenic indicator reagent is continuously released from a reagent zone in the element to an adjacent reaction zone containing the fluid sample containing the analyte and possible interferent. The rate at which reagent is continuously released to the reaction zone characteristically produces a color response attributable to the selective interaction of indicator with analyte and reduced—often eliminated—interaction of indicator with interferents.

The invention set forth below pertains to an element comprising, in part, a configuration wherein a reaction zone overlies or is adjacent to a reagent zone. A similar configuration is disclosed in the aforementioned U.S. Pat. Nos. 3,992,158 and 4,042,335. In contrast to the disclosure of these patents, however, the present reagent zone is impermeable to analytes such as albumin. Hence, the analyte is retained in the reaction zone, while reagent, under the influence of fluid in the sample, migrates into the reaction zone to produce a detectable change.

In one aspect, this invention comprises a multizone dry analytical element having a reaction zone for receiving an aqueous fluid to be subjected to an assay for the selective determination of an analyte in the fluid, which fluid contains the analyte, the element comprising:

(a) means forming a dry reagent zone impermeable to the analyte and interferents to an assay for the analyte, said reagent zone being in fluid contact with the reaction zone when the element is contacted with a sample of the fluid, the reagent zone comprising a chromogenic indicator reagent composition which interacts with analyte and interferents to produce a color response, and (b) means responsive to contact of the sample with the element for continuously releasing the reagent composition from the reagent zone to the reaction zone at a rate sufficient to produce an analyte color response corresponding to
 (1) the interaction of indicator with analyte, and
 (2) reduced interaction of indicator with interferents.

In a preferred embodiment, an analytical element for the selective determination of albumin in aqueous fluids containing albumin and possible protein interferents to an albumin assay is set forth. In the albumin selective element, the reagent comprises a chromogenic indicator such as BCG, and the element also contains a buffer, for example, in the reagent zone. In accordance with the invention, the rate at which the chromogenic indicator reagent is released is sufficient to produce an albumin color response corresponding to the interaction of indicator with albumin and reduced interaction of indicator with protein interferents. Most preferably, the rate of reagent release is sufficient to produce an albumin response corresponding to interaction of indicator substantially only with albumin in which case essentially no interaction of indicator with protein interferents occurs. Unlike the prior art, particularly with regard to albumin assays of undiluted body fluids, the present element exhibits albumin selectively for relatively long periods of time, for example, up to three minutes or more.

A presently preferred means for effecting continuous release of reagent as defined comprises a polymer that serves as binder in the reagent zone. This polymer is responsive to the application of a fluid sample to the element by continuously releasing indicator reagent from the reagent zone to the reaction zone according to the above-defined rate.

In another aspect of this invention, a method for the selective determination of an analyte in aqueous fluids containing the analyte and possible interferents to the analyte assay comprises contacting a sample of the fluid with the element to produce an analyte color response as defined. Such response is then employed to determine the analyte such as by comparison with suitable calibrators.

In yet another aspect of the invention, a method for the reduction of interference to an analyte assay comprises contacting an element composed of the above-defined reaction and reagent zones with a sample of the fluid to produce an analyte color response as defined above and determining the analyte.

DETAILED DESCRIPTION OF THE PREFERRED EMBODIMENTS

The present invention facilitates selective determination of an analyte such as albumin or magnesium in aqueous fluids such as serum, urine and other fluids using a multizone dry analytical element defined below. Biased determinations arising from interferents, if present, such as globulins or transferrin, in the case of an albumin assay, or calcium in the case of a magnesium assay, are effectively minimized or eliminated. To this end, the present inventors have determined that continuous release of a chromogenic indicator reagent at a defined rate from one zone in the element to another zone containing the analyte and possible interferents provides improved analyte selectivity within reasonable periods of time.

The concept of continuous release of indicator reagent to a reaction zone is applicable to the selective determination of various analytes. Accordingly, magnesium can be determined selectively with the indicator dye [1-(1-hydroxy-2-naphthylazo)-2-hydroxy-5-nitro-4-naphthalene sulphonic acid sodium salt] in the presence of calcium as an interferent. This dye is available commercially from Ciba-Geigy Corp. under the tradename Eriochrome ® Black T (EBT). Alternatively, magnesium can be determined with Titan yellow dye. The present invention is also employed to selectively determine albumin in the possible presence of protein interferents to an albumin assay. In the albumin assay, a reagent composition comprising a chromogenic indicator is employed. The reagent is buffered as defined below. Although this invention contemplates any assays for a variety of analytes and potential interferents, the present invention is set forth more particularly below in the context of an albumin assay for purposes of illustration. Corresponding elements for other analytes operate in the same manner.

Elements according to the present invention are multizoned. The reaction zone and reagent zone, as well as any other optional zones, are separate and distinct from one another. Such zones, for example, are horizontally disposed layers or vertically disposed bands depending on whether sample application is from the side or the top of the element. The zones are optionally discontinuous reagent zones within a continuous reaction zone. Preferably, the zones are in the form of layers.

The reaction zone of the defined element serves several functions. Initially, the zone receives and contains a sample of fluid containing, for example, albumin to be analyzed and protein interferents. Since the reagent zone is impermeable to the albumin and protein interferents, they are effectively retained in the reaction zone. Portions of the liquid component in the sample, however, pass from the reaction zone into the reagent zone, causing chromogenic indicator reagent to be continuously released into the reaction zone. Interaction of the reagent with albumin follows to produce an albumin color response as defined herein.

The reaction zone optionally serves as a spreading zone to which a fluid sample is applied or contacted, and within which the sample is uniformly spread. Alternatively, a separate spreading zone in fluid contact with the reaction zone is employed to receive and uniformly distribute the fluid sample to the reaction zone.

Suitable reaction zones include isotropically porous layers as disclosed in U.S. Pat. No. 3,992,158 issued Nov. 16, 1976 to E. P. Przybylowicz and A. G. Millikan, incorporated herein by reference. Such layers are prepared using a variety of components. In one aspect, particulate materials are used to form the layers wherein isotropic porosity is created by interconnected spaces between the particles. Alternatively, such layers are prepared using isotropically porous polymers, for example "blush" polymers as disclosed in U.S. Pat. No. 3,992,158. With regard to the present invention, however, the use of pigments such as $TiO_2$ in the reaction zone is to be avoided if such pigments mask the color response that occurs in the reaction zone, as described below.

A preferred reaction zone comprises an isotropically porous layer containing colloidal materials derived from natural or synthetic polymers. Microcrystalline cellulose, which is commercially available from FMC Corporation under the name Avicel ®, is one example of such colloidal material which is preferred for use in the present invention. Examples of other materials include silica and diatomaceous earth.

Reaction zones comprising bead layers as described in copending U.S. patent application Ser. No. 973,669 filed Dec. 27, 1978 in the names of Z. R. Pierce and D.

S. Frank, incorporated herein by reference, are also usefully employed in multizone elements of the present invention. Such bead layers contain particles held together by a low amount of adhesive uniquely localized between adjacent particles where the particles are in closest proximity.

The reagent zone of the present invention is, before use, essentially dry. That is, the reagent zone is fluid-free, facilitating storage of the element for long periods of time in a relatively small amount of space. Also, the reagent layer is impermeable to analyte and interferents but otherwise permeable to the remaining liquid in the fluid sample applied to the reaction zone. Thus, when a fluid sample is applied, fluid contact between the two zones is established and chromogenic indicator reagent is continuously released to the reaction zone to bind to the analyte such as albumin.

The present reagent zone is rendered impermeable to analyte and interferents by various means. For example, in the case of albumin, reagent zones having pores with a diameter smaller than that of albumin and protein interferent molecules prevent the passage of those molecules into the reagent zone. On the other hand, such as in the determination of magnesium in the presence of calcium interferent having molecular diameters which are extremely small, chelating or ballasting agents with high molecular weights are desirably employed. Such agents interact with the magnesium and calcium to produce molecules with diameters larger than the pores in the reagent zone, effectively rendering the reagent zone impermeable to that analyte and interferent. Useful chelating agents for magnesium and calcium include addition polymers having chelating groups appended to the polymer backbone.

Reference herein to fluid contact between the reaction and reagent zones in the defined analytical element identifies the ability of a fluid to pass in such element between superposed or adjacent regions of the reaction zone and reagent zone. Although the two zones in fluid contact are preferably contiguous, they are optionally separated by intervening zones. However, such intervening zones and any other optional zones included in the element are themselves in fluid contact with each other and with the reaction and reagent zones so as not to interrupt the passage of fluid between the reaction and reagent zones.

Reagent zones according to the present invention contain a reagent composition comprising a chromogenic indicator which interacts with analyte (such as albumin) and interferents (such as protein) to produce a color response. Such zones include a matrix in which the reagent composition is distributed. The choice of matrix material is variable, except when the matrix is selected as the means for continuously releasing the reagent into the reaction zone as defined below. When not so selected, however, the matrix generally includes non-proteinaceous hydrophilic materials including both naturally occurring and synthetic substances. Examples of such materials are polysaccharides such as agarose, poly-vinyl compounds such as poly(vinyl alcohol), and hydro-philic cellulose derivatives.

Chromogenic indicators are employed in the reagent zone to determine the analyte, such as albumin, in aqueous fluids. Suitable indicators for albumin are those that are known for their use in solution or in bibulous carriers to determine pH colorimetrically. Such indicators produce a color response corresponding to the pH of sample solutions. Many indicators exhibit so-called "protein error" which amounts to a color response of indicator by interaction with protein in solution thus giving rise to erroneous pH determinations. However, by buffering the indicator, color response attributable to pH changes is avoided, thereby rendering the protein error useful in the determination of protein such as albumin. The buffer is either included in the reaction zone in the reagent zone, in both zones or in a separate buffered zone. Preferably, the buffer is included as part of the reagent zone. By using buffer, the pH of samples undergoing analysis is maintained constant, or at least maintained outside of the pH range in which the indicator normally responds to pH changes. In practicing the invention in its broader aspects the use of buffer is optional. In practicing an albumin assay, the foregoing principle of buffering the indicator is preferably employed.

Chromogenic indicators that are used successfully in the present reagent zone are indicators disclosed by I. M. Kolthoff in *Acid-Base Indicators* published by The MacMillan Company, New York (1937), particularly those exhibiting protein error as shown on pages 350–353. Examples of such indicators are bromcresol green (BCG), methyl red, bromphenol blue, bromcresol purple, bromthymol blue, phenol red, cresol red, thymol blue, cresolphthalein, and those indicators disclosed in U.S. Pat. No. 3,438,737 issued Apr. 15, 1969 to R. L. Atkinson et al., columns 3 and 4. Indigo dyes such as indigo carmine are also usefully employed in the practice of the present invention. Of these indicators, the sulphonphthalein indicators such as bromcresol green and bromcresol purple are preferred in the assay for albumin. In the assay for analytes other than albumin, e.g., magnesium, indicators such as Eriochrome Black T ® or Titan yellow are suitable for use.

The amount of chromogenic indicator employed in the present reagent zone is sufficient to interact with the largest anticipated amount of analyte in the sample of aqueous fluid which is to be tested by the present element. In the assay for albumin, it is preferred that the reagent zone comprise sufficient indicator to interact with and produce a linear color response with concentrations of albumin up to about 10 g/dL or higher, most preferably up to 5 g/dL. A linear color response, as used herein, signifies a color response that increases linearly with time during a predetermined time frame after application of the sample. For example in the albumin assay, such time frame is from about one to about three minutes after sample application. Also, in the albumin assay, BCG indicator is employed in the reagent zone at a concentration range from about 0.2 g/m$^2$ to about 3.0 g/m$^2$, preferably about 0.5 to about 1.5 g/m$^2$ which has been determined to produce reasonably linear response using 10 μL fluid samples containing up to 5 g/dL albumin. A concentration of about 1.0 g/m$^2$, in this regard, is most preferred and corresponds to a BCG concentration of about 15 millimoles per liter of such fluid. Accordingly, for different sample volumes, adjustment up or down form 1.0 g/m$^2$ coverage in the reagent zone to maintain the preferred 15 millimoles per liter is desirable.

Various known types of buffers are useful to maintain the assay for albumin isohydric (i.e., substantially constant in pH), and thus avoid pH effects in the color response. The amount and type of buffer depends upon the nature of the fluid being tested and the type of chromogenic indicator employed. It is also preferable to buffer to a non-alkaline pH. Thus, for a given chromogenic indicator with a known pH-sensitive range, one preferably selects a buffer composition that will bring the assay to a substantially constant pH below the indicator pH-sensitive range. Such a buffer composition, in this instance, comprises acids or acids together with their salts. Suitable acids that are used, singly or in combination with their salts or other listed acids include low molecular weight carboxylic acids such as malic acid, lactic acid, succinic acid, malonic acid, citric acid, and tartaric acid. Other acid buffers are disclosed in U.S. Pat. No. 3,438,737 issued Apr. 15, 1959 to R. L. Atkinson et al. Malic acid is a preferred buffer.

BCG is a preferred chromogenic indicator employed in the present reagent composition for an albumin assay. For the determination of albumin in neat (undiluted) serum using BCG, the amount of buffer is preferably that amount which will maintain a sample of the serum at a pH within the range from about 2.0 to about 4.0, most preferably at a pH of about 3.2. For a 10 $\mu$L volume of sample serum, approximately 10.8 g/m$^2$ of malic acid buffer has been determined to provide a pH of about 3.2.

The reagent composition also optionally includes components which do not adversely affect the capability of the chromogenic indicator to interact with the analyte as discussed above. One such optional component is a non-ionic surfactant. Representative surfactants include alkylphenoxy polyethoxy ethanols available commercially, for example, from Rohm and Haas Co. under the Triton ® tradename series such as Triton X-100 ® and Triton X-405 ®; polyoxyethylene oleyl ether such as Brij 98 ® sold by Atlas Chemical Industries; polyoxyethylene sorbitan monolaurate such as Tween 20 ® also sold by Atlas Chemical Industries; and (p-nonylphenoxy)glycerol sold by Olin Matheson Corp. under the tradename Surfactant 10G ®.

The element in accordance with the present invention further includes means for continuously releasing the defined reagent composition from the reagent zone to the reaction zone (hereinafter referred to as release means). Such continuous release, moreover, occurs in response to contact of the element with a fluid sample. The rate of reagent release is chosen so as to produce a color response in the reaction zone corresponding to the interaction of the chromogenic indicator in the reagent with analyte and reduced interaction of the indicator with interferents.

Examples of foregoing release means include several alternative embodiments. In a presently preferred mode, the release means comprises a polymeric binder for the reagent layer containing a polymer that has an affinity for the defined reagent composition. This affinity is slowly disrupted in response to application of a fluid sample to produce continuous reagent release. Preferred polymers exhibiting such reagent release characteristics comprise water-soluble addition polymers, most preferably vinyl polymers such as those composed of acrylamide and/or vinylpyrrolidone recurring units, particularly poly(vinylpyrrolidone-co-acrylamide) containing from about 20 to about 80 weight percent vinylpyrrolidone and from 80 to about 20 weight percent acrylamide. Especially preferred are copolymers of acrylamide and vinylpyrrolidone prepared from a monomer blend composed of equal weight amounts of acrylamide and vinylpyrrolidone monomers.

Useful continuous release of reagent has also been achieved with cellulosic polymers such as hydroxyethylcellulose as the reagent layer binder.

A procedure for screening potential polymers for their use as release means entails forming a multilayered analytical element comprising a reaction layer overlying a reagent layer carried by a support. The reagent layer includes the potentially useful polymer and the defined reagent composition dispersed in the polymer. The reaction layer of the element is then contacted with an aqueous control fluid containing a known amount of albumin. Alternatively, the control fluid is a sample of a solution composed of 0.9% (by weight) NaCl, 0.033% CaCl$_2$, and 0.3% KCl and the balance water (this solution is commonly referred to as Ringer's solution). The color response, developed in the reaction layer, measured as the reflection density ($D_R$) is then monitored versus time until a maximum $D_R$ is reached. If the $D_R$ value reaches its maximum immediately, that is, within less than thirty seconds, the polymer being studied is not considered useful to continuously release reagent as defined. However, if a maximum $D_R$ is reached in more than thirty seconds, preferably within 1-10 minutes, the polymer is useful. In conducting evaluations pursuant to the present invention, it is demonstrated, for example, that polymers such as agarose are not capable of such continuous release, all of its dispersed reagent being essentially released instantaneously (i.e., in less than thirty seconds) upon application of the control fluid.

The principle of continuous release, as used herein, denotes a gradual addition of reagent to the reaction zone of the present analytical element. It is to be distinguished from delayed release of reagent which contemplates a time period after application of a sample fluid before all available reagent is immediately released to the sample fluid. Continuous release is essentially synonymous with "metering" in the sense that portions of a material are supplied in a regulated amount and rate from a larger reservoir (i.e., the reagent zone) of such material, as opposed to supplying the entire reservoir instantaneously. Furthermore, in conducting evaluations pursuant to this invention, it has been found that certain polymers, when used as the matrix for the reagent zone, not only exhibited continuous release as defined, but also exhibited a so-called lag-phase immediately after application of the sample fluid. That is, continuous release of reagent was delayed, or at least significantly lowered in rate, for the first 30 to 45 seconds after sample application. The term "continuous release" is intended to include the combination of a lag-phase and subsequent continuous release of the indicator.

Reference has been made above to continuous release means composed of a certain polymeric matrix for the reagent zone in a preferred embodiment. Other embodiments to achieve the same purpose include, for example, continuous release zones, impermeable to albumin and protein interferents, interposed between the reaction and reagent zones so as to maintain fluid contact between the latter two zones. When the element containing such continuous release zone is contacted with a sample of fluid, the release zone cooperates with the reagent zone to provide continuous reagent release to the reaction zone. Continuous release zones comprise, for example, matrices composed of the continuous release polymers defined above for use in the reagent zone. Accordingly, such polymers include, for example, water-soluble addition polymers, preferably vinyl polymers such as those comprising vinylpyrrolidone and/or acrylamide recurring units. Screening of polymers for potential use in the continuous release zone entails substantially the same procedure employed to screen for useful continuous release polymers for the reagent zone matrix. In this instance, however, the proposed element includes a continuous release zone interposed between reaction and reagent zones.

The release means is also characterized by exhibiting a rate of release that produces an analyte color response corresponding to the interaction of indicator with analyte and reduced interaction with interferents. The demonstration of such analyte color response in a proposed analytical element is facilitated by comparison with an otherwise identical element containing essentially no continuous release means (hereinafter referred to as control element). In this comparison, two of the control elements and two of the proposed elements are employed. The first control element is contacted with a fluid sample, such as neat serum, containing analyte, to produce a first color response that is recorded against time. The second control element is contacted with a sample of the same fluid to which an arbitrary, usually 5% by weight interferent ($\gamma$-globulin in an albumin assay), has been added to produce a second color response that is also recorded against time. The difference between the two responses at any selected point in time is attributable to the presence of added interferent (globulin). As previously noted, the present invention reduces, and in many cases eliminates, this difference. Accordingly, the two proposed elements are contacted with the analyte fluid sample and analyte/added-interferent (globulin) fluid sample, respectively, to produce two color response curves with time. In accordance with the present invention, it has been found that the difference between the response curves for the proposed element is inherently less for extensive periods of time after application of a fluid sample compared to the control element. By appropriate selection of components and coating levels, the difference between color responses using the proposed elements can be substantially eliminated, preferably for periods of time of at least one minute, most preferably up to 3 minutes. After those periods of time, the difference is advantageously reduced but not eliminated. Eventually, a transition point in time is reached where the color response difference for the proposed element is essentially the same as the difference for the control element. Therefore, in using the proposed element, one selects a color response that occurs prior to the transition point, preferably when no difference occurs, as above determined. Such color response is thereafter employed for the determination of analyte.

The rate of reagent release is influenced by several factors including, for example, the polymer chosen, the reagent zone thickness (for constant levels of chromogenic indicator), chromogenic indicator levels and buffer levels when buffer is included in the reagent zone. How these variables are manipulated is a matter of choice within the skill of the art. It has been found, for example, that the rate of release in certain instances for addition homopolymers of acrylamide is significantly effected by varying the buffer level in the reagent zone containing the homopolymer. In particular, lowering the buffer level increased the rate of release from such reagent zone.

The analytical elements are self-supporting or carried on a support. Useful support materials include a variety of polymeric materials, such as cellulose acetate, poly- (ethylene terephthalate), polycarbonates and polyvinyl compounds, such as polystyrenes. A support of choice for any particular element is compatible with the intended mode of analyte detection. Preferred supports include radiation-transmissive support materials that transmit electromagnetic radiation of a wavelength or wavelengths within the region between about 200 nm and about 900 nm, as well as radiation due to radioactivity. When an element includes a support, the reagent zone is usually interposed between the support and the reaction zone, which is preferably the outermost layer in the element.

A variety of different elements, depending on the method of analysis, can be prepared in accordance with the present invention. Elements are configured in a variety of forms, including elongated tapes of any desired width, sheets or slides.

The prepared elements are placed in use by applying a sample of liquid under analysis to the element. When the reaction zone also serves as a spreading zone, an applied sample contacts the reaction zone prior to contacting the reagent zone and first contacts such reaction zone at its surface furthest removed from such reagent zone. Because analytical accuracy of the present elements is not substantially diminished by variations in the volume of applied samples, sample application by hand or machine is acceptable. For reasons of convenience in detecting an analytical result, however, reasonable consistency in sample volume is desirable.

In an analytical procedure using the present elements, the element is taken from a supply roll, slide packet or other source and positioned to receive a free drop, contact spot or other form of liquid sample, such as from an appropriate dispenser. After sample application, and desirably after the liquid sample has been taken up by the reaction zone, the element is optionally exposed to conditioning, such as incubation or heating to facilitate obtaining the test result.

Measurement of the analyte color response is obtained, usually by passing the element through an area in which suitable apparatus for reflection or transmission spectrophotometry is provided. Such apparatus serves to direct a beam of energy, such as light, through the support and the reagent zone and into the reaction zone. The light is then reflected back from the reaction zone to a detecting means or passes through the element to a detector, in the case of transmission detection. Alternatively, the beam of energy can be directed initially into the reaction zone for reflection or transmission detection in an analogous manner. Use of reflection spectrophotometry is preferred. Generally electromagnetic radiation in the range of from about 200 to about 900 nm has been found useful for such measurements, although it is possible to use any radiation to which the element is permeable and which is capable of quantifying the analyte color response in the reaction zone. Various known calibration techniques are useful to provide calibration curves for the analysis.

Ordinarily, samples of fluid employed with the present element contain both the analyte to be determined and interferents. Accordingly, if interferents are certain to be absent, the continuous release means defined above can be dispensed with. However, in practice such certainty entails a potentially expensive and time-consuming analytical assessment of the fluid samples for interferents. It is an advantage, therefore, that the present element comprises the continuous means of release as defined without regard to the presence of interferents in the fluid under analysis. In this manner, the continuous release of reagent serves not only to reduce the undesirable effects of any interferents, but also serves as an assurance against the possible presence of interferents even though they may be absent. The state of the art is thus advanced by providing certainty against interference and dispensing with the need to assay for the presence of the interfering substances.

The following Examples are presented.

EXAMPLES

In the ensuing preparations and examples, the following materials and procedures were employed:

Human serum was supplied from hospitals. Samples not immediately used were kept frozen at $-80°$ C.

Human Pentex albumin, human Pentex alpha and gamma globulin fractions were obtained from Miles Laboratories, Inc., Elkhart, Ind.

Poly(acrylamide-co-N-vinyl-2-pyrrolidone), 50:50 monomer weight ratio, was prepared as in Example 1 of U.S. Pat. No. 4,132,528 issued Jan. 2, 1979 to J. N. Eikenberry et al. (hereinafter referred to as polymer 1).

Poly(acrylamide) was purchased from Eastman Organic Chemicals, Rochester, N.Y. (hereinafter referred to as polymer 2).

Sea plaque agarose was purchased from Marine Colloids, Inc.

Microcrystalline cellulose was purchased as Avicel ® from FMC Corp.

(P-nonylphenoxy) glycerol was purchased as Surfactant 10G ® from Olin Matheson Corp.

All other chemicals were obtained from Eastman Kodak Company, and were reagent grade, unless otherwise indicated.

Spectrophotometric measurements were made using a Cary 118 or Beckman 25 instrument. Reflectance measurements were made using appropriate reflectometers with interference filters at 630 nm when di-protonated BCG was monitored and at 420 nm when mono-protonated BCG was monitored. These instruments were used to measure the reflection density, $D_R$, of a beam of light transmitted through the elements described in the examples and reflected back by the layers in the element.

Element Formation

Elements referred to as Elements 41–46 in the following formulations were prepared and used in the examples. The coating levels are in g/m$^2$ of the material indicated.

| Reaction Layer | Microcrystalline Cellulose Poly(vinylpyrrolidone) | | | | 53.80 g/m$^2$ 1.35 g/m$^2$ | | |
|---|---|---|---|---|---|---|---|
| | | 41 | 42 | 43 | 44 | 45 | 46 |
| | Polymer 1 | 32.28 | — | — | 16.14 | — | — |
| | Polymer 2 | — | 32.28 | 16.14 | — | — | — |
| Reagent | Agarose | — | — | — | — | 16.14 | 32.28 |
| Layer | BCG | 1.08 | 1.08 | 0.54 | 1.08 | 1.08 | 1.08 |
| | Malic Acid | 10.8 | 5.4 | 2.7 | 5.4 | 5.4 | 10.8 |
| | Surfactant 10G ® | 0.32 | 0.32 | 0.32 | 0.32 | 0.32 | 0.32 |
| Support | | polyethylene terephthalate film | | | | | |

EXAMPLE 1

Screening for Potentially Useful Release Polymers

In this example, the reagent release capability of various polymers was evaluated when used as a binder for the reagent layer. Elements 44 and 45 were each spotted with 10 µL samples of solution containing 5.0 g/dL human Pentex albumin. The $D_R$ at 630 nm of Element 45 containing agarose reached a maximum almost immediately and within less than 30 seconds, indicating that the agarose evaluated was not a useful release polymer. In Element 44, however, the $D_R$ at 630 nm increased gradually and reached a maximum after about 4 minutes indicating that polymer 1 is a useful release polymer.

The polymers employed as reagent layer binder in Elements 41, 42 and 43 were also evaluated for their reagent release capability except that reagent release was stimulated by contact of each element with 10 µL samples of Ringer's solution. $D_R$ values at 420 nm were recorded versus time. In Element 41, a maximum $D_R$ was reached after about 2 minutes indicating useful release.

In Element 42, no increase in $D_R$ was observed for approximately the first $\frac{1}{2}$ minute after which $D_R$ slowly increased to a maximum after about 4 minutes. Polymer 2, therefore, as used in Element 42, exhibits a desirable lag-phase in combination with continuous release as defined.

In Element 43, a maximum $D_R$ was reached after about 45 seconds indicating useful release.

EXAMPLE 2

Effect of Continuous Release on Globulin Interference

Samples of pooled human serum were prepared containing added globulin in the following amounts: 0 (control); 2% alpha globulin; 4% alpha globulin and 2% gamma globulin. 10 µL aliquots of these samples were applied to the reaction layer of Element 41, one aliquot to an element. $D_R$ at 630 nm was monitored versus time for 5 minutes at 37° C. The $D_R$ values during the first two minutes for elements contacted with serum containing added globulin were essentially identical to the $D_R$ values for the element contacted with the control indicating essentially no interfering color response from the added globulins during this time period.

EXAMPLE 3

Comparison of the Effect of Continuous Reagent Release and Instantaneous Reagent Release of Globulin Interference Elements 41 and 46 (Control A) were contacted with various samples described below. The $D_R$ values exhibited at 630 nm by the elements at 1 minute read times were compared.

A third, single-zone element (Control B) was prepared composed of Whatman-3 Filter paper imbibed with 0.22 g/m$^2$ BCG; 10.76 g/m$^2$ malic acid and 0.3 g/m$^2$ Surfactant 10G ®. The amount of BCG imbibed in the paper was one-fifth the amount of dye employed in element 41. Such amount corresponds approximately to the amount of BCG released in Element 41 from the reagent layer to the reaction layer during the first minute after contact with a liquid sample.

The elements were each contacted with 10 µL samples of human Pentex albumin calibrator solutions having concentrations of 1.7, 2.5 and 5.0 g/dL albumin respectively, and the $D_R$ value at 630 nm exhibited by each element at one minute was recorded. The procedure was repeated except that each calibrator solution contained an additional 5% gamma globulin. For each element a bias attributable to the color response from interaction of BCG with gamma globulin was determined by computing the percentage increase of the $D_R$ for samples containing globulin over the $D_R$ of the sample containing no globulin. Results are shown in Table I.

TABLE I

| Element | Albumin Amount (g/dL) | $D_R$ | Albumin & Globulin $D_R$ | % Bias |
|---|---|---|---|---|
| 41 | 1.7 | .71 | .84 | 18.3 |
|  | 2.5 | .88 | 1.0 | 13.6 |
|  | 5.0 | 1.18 | 1.24 | 5 |
| 46 (Control A) | 1.7 | 1.0 | 1.7 | 70 |
|  | 2.5 | 1.3 | 1.9 | 46 |
|  | 5.0 | 1.7 | 2.4 | 41 |
| Imbibed paper (Control B) | 1.7 | .17 | .42 | 147 |
|  | 2.5 | .26 | .46 | 77 |
|  | 5.0 | .42 | .58 | 38 |

The larger bias percentages exhibited by Element 46 compared to Element 41 clearly show the advantage of continuous release of reagent from the reagent layer, with both reagent layers containing the same initial amount of reagent. The bias percentages of Element 41 and the imbibed paper element substantiates the advantage of continuous over the instantaneous use of equal amounts of BCG.

EXAMPLE 4

Reduction of Calcium Interference In an Assay for Magnesium.

Analytical Elements 41 and 46 are prepared except that BCG is replaced with the initiator dye Eriochrome Black T ®. A polymeric chelating agent for magnesium and calcium is also included in the reaction layer to render the reagent layer impermeable to magnesium and calcium.

10 μl aqueous samples containing in one instance magnesium and in another instance magnesium and calcium as an added interferent are applied to the reaction layers to generate appropriate color response curves against time. The difference between the response curves, i.e., magnesium curve and magnesium plus added calcium curve, is substantially less for Element 41 than the difference between the color response curves generated for Element 46 (control). Accordingly, calcium interference in a magnesium assay is effectively reduced in accordance with the present invention.

The invention has been described in detail with particular reference to preferred embodiments thereof, but it will be understood that variations and modifications can be effected within the spirit and scope of the invention.

What is claimed is:

1. A multizone dry analytical element comprising
   (a) reaction zone for receiving an aqueous fluid to be subjected to an assay for the selective determination of an analyte in the fluid, which fluid contains said analyte;
   (b) means forming a dry reagent zone impermeable to said analyte and interferents to an assay for said analyte, said reagent zone being in fluid contact with said reaction zone when said element is contacted with a sample of said fluid, said reagent zone including a reagent composition comprising a chromogenic indicator which interacts with said analyte and interferents to produce a color response; and
   (c) release means responsive to contact of said sample with said element for continuously releasing said reagent composition from said reagent zone to said reaction zone at a rate sufficient to produce an analyte color response corresponding to:
      (1) the interaction of said indicator with said analyte, and
      (2) reduced interaction of said indicator with interferents.

2. A multizone dry analytical element as in claim 1 wherein said release means comprises a polymeric binder for said reagent composition, which binder is responsive to contact of a sample of said fluid with said element to effect said continuous release of reagent.

3. A multizone dry analytical element as in claim 2 wherein said polymeric binder comprises a water-soluble addition polymer.

4. A multizone dry analytical element as in claim 3 wherein said addition polymer is selected from the group consisting of vinylpyrrolidone, acrylamide and vinylpyrrolidone-acrylamide recurring units.

5. A multizone dry analytical element comprising
   (a) reaction zone for receiving, and for the selective determination of magnesium in, an aqueous fluid sample containing magnesium;
   (b) means forming a dry reagent zone impermeable to magnesium and calcium, in fluid contact with said reaction zone when said element is contacted with said sample, said reagent zone comprising a reagent composition comprising a chromogenic indicator which interacts with magnesium and calcium to produce a color response; and
   (c) release means responsive to contact of said sample with said element for continuously releasing said reagent composition from said reagent zone to said reaction zone at a rate sufficient to produce a magnesium color response corresponding to:
      (1) the interaction of said indicator with magnesium, and
      (2) reduced interaction of said indicator with calcium.

6. A multizone dry analytical element as in claim 5 wherein said chromogenic indicator is Titan yellow or [1-(1-hydroxy-2-naphthylazo)-2-hydroxy-5-nitro-4-naphthalene sulphonic acid sodium salt].

7. A multizone dry analytical element as in claim 5 wherein said release means comprises a polymeric binder for said reagent composition, which binder is responsive to contact of a sample of said fluid with said element to effect said continuous release of reagent.

8. A multizone dry analytical element as in claim 7 wherein said polymeric binder comprises a water-soluble addition polymer.

9. A multizone dry analytical element as in claim 8 wherein said addition polymer is selected from the group consisting of vinylpyrrolidone, acrylamide and vinylpyrrolidone-acrylamide recurring units.

10. A multizone dry analytical element comprising
   (a) reaction zone for receiving, and for the selective determination of albumin in, an aqueous fluid sample containing albumin;
   (b) a buffer
   (c) means forming a dry reagent zone, impermeable to albumin and protein interferents to an assay for albumin, said reagent zone being in fluid contact with said reaction zone when said element is contacted with said sample, said reagent zone comprising a reagent composition containing a chromogenic indicator which interacts with albumin and protein interferents in the presence of said buffer to produce a color response, and (d) means responsive to contact of said sample with said element for continuously releasing said reagent composition from said reagent zone to said reaction zone at a rate sufficient to produce an albumin color response corresponding to the interaction of said indicator with albumin and reduced interaction of said indicator with protein interferents.

11. A multizone dry analytical element as in claim 10 wherein said chromogenic indicator is a sulphonphthalein dye.

12. A multizone dry analytical element as in claim 11 wherein said rate of continuous release is sufficient to produce a color response corresponding to the interaction of said indicator substantially only with albumin.

13. A multizone dry analytical element as in claim 11 or 12 wherein said chromogenic indicator is bromcresol green and said buffer is provided in an amount sufficient to maintain said fluid at a pH lower than that of the pH range in which said indicator is pH-sensitive.

14. A multizone dry analytical element comprising a reaction zone for receiving, and for the selective determination of albumin in, an aqueous fluid sample containing albumin; means forming a dry, polymeric reagent zone, impermeable to albumin and protein interferents to assay for albumin, said reagent zone being in fluid contact with said reaction zone when the reaction zone is contacted with said sample; said reagent zone comprising, in a polymeric binder, a reagent composition comprising a buffer and a chromogenic indicator which interacts with albumin and protein interferents in the presence of said buffer to produce a color response, said polymer being responsive to contact of said sample with said element for continuously releasing said reagent composition from said reagent zone to said reaction zone at a rate sufficient to produce an albumin color response corresponding to the interaction of said indicator with albumin and reduced interaction of said indicator with protein interferents.

15. A multizone dry analytical element as in claim 14 wherein said polymeric binder comprises a water-soluble addition polymer, and wherein said chromogenic indicator is water soluble.

16. A multizone dry analytical element as in claim 15 wherein said addition polymer is selected from the group consisting of vinylpyrrolidone, acrylamide and vinylpyrrolidone-acrylamide recurring units.

17. A multizone dry analytical element as in claim 15 or 16 wherein said chromogenic indicator is a sulphonphthalein dye.

18. A multizone dry analytical element as in claim 17 wherein said rate of continuous release is sufficient to produce an albumin color response corresponding to the interaction of said indicator substantially only with albumin.

19. A multizone dry analytical element as in claim 18 wherein the interaction of said indicator substantially only with albumin occurs for at least a minute after contact of said fluid sample with said element.

20. A multizone dry analytical element as in claim 18 wherein said indicator is bromcresol green and said buffer is present in an amount sufficient to maintain said fluid at a pH lower than that of the pH range in which said indicator is pH-sensitive.

21. A multizone dry analytical element as in claim 20 wherein the amount of bromcresol green released from said reagent zone is sufficient to produce an albumin color response that varies linearly with albumin concentrations up to 5 g/dL in said sample.

22. A multizone dry analytical element as in claim 20 wherein the amount of said bromcresol green in said reagent layer is sufficient to provide a concentration of at least 15 millimoles bromcresol green per liter of said fluid.

23. A multizone analytical element as in claim 1, 5, 10 or 14 wherein said reaction and reagent zones are separate and distinct layers.

24. A multizone analytical element as in claim 23 wherein said element comprises, in sequence, a spreading alayer, said reaction layer and said reagent layer.

25. A method for the selective determination of an analyte in an aqueous fluid containing said analyte, said method comprising (a) contacting a sample of said fluid with a reaction zone of a multizone dry analytical element having a reaction zone in fluid contact with a dry reagent zone; said reagent zone being impermeable to said analyte and interferents to an assay for said analyte and includes a reagent composition comprising a chromogenic indicator which interacts with said analyte and interferents to produce a color response; and said contacting causes release of said reagent composition from said reagent zone to said reaction zone at a rate sufficient to produce an analyte color response corresponding to (1) the interaction of said indicator with said analyte, and (2) reduced interaction of said indicator with interferents; and (b) determining said analyte from said analyte color response.

26. A method for the selective determination of albumin in an aqueous fluid containing albumin, said method comprising (a) contacting a sample of said fluid with reaction layer of a multilayer dry analytical element having a reaction layer in fluid contact with a dry reagent layer; said reagent layer being impermeable to albumin and protein interferents to an assay for albumin and includes in a polymeric binder, a reagent composition comprising a buffer and a chromogenic indicator which interacts with albumin and protein interferents in the presence of said buffer to produce a color response, and said contacting causes said polymer to release said reagent composition from said reagent layer to said reaction layer at a rate sufficient to produce an albumin color response corresponding to the interaction of said indicator with albumin and reduced interaction of said indicator with protein interferents; and (b) determining albumin from said albumin color response.

27. A method for reducing protein interference in an analytical determination for albumin in a fluid sample containing albumin and protein interferents to an assay for albumin, said method comprising (a) contacting a sample of said fluid with a reaction layer of a multilayer dry analytical element having a reaction layer in fluid contact with a dry reagent layer; said reagent layer being impermeable to albumin and said protein interferents and includes in a polymeric binder, a reagent composition comprising a buffer sufficient to maintain said fluid at a non-alkaline pH and a sulphonphthalein chromogenic indicator which interacts with albumin and protein interferents in the presence of said buffer to produce a color response, and said contacting causes said polymer to release said reagent composition from said reagent layer to said reaction layer at a rate sufficient to produce an albumin color response corresponding to the interaction of said indicator with albumin and reduced interaction of said indicator with protein interferents; and (b) determining albumin from said albumin color response.

* * * * *